United States Patent [19]
Gurol

[11] Patent Number: 6,102,213
[45] Date of Patent: Aug. 15, 2000

[54] BEVERAGE FILTER FOR REDUCING COFFEE ACIDITY

[75] Inventor: Ismail Macit Gurol, Seattle, Wash.

[73] Assignee: Tamer International, Ltd., Seattle, Wash.

[21] Appl. No.: 09/183,968

[22] Filed: Oct. 30, 1998

Related U.S. Application Data

[62] Division of application No. 08/577,147, Dec. 22, 1995, Pat. No. 5,853,787.

[51] Int. Cl.[7] .............................. B01D 24/00; A23F 5/00
[52] U.S. Cl. ...................... 210/506; 210/500.1; 426/433; 426/590; 426/595
[58] Field of Search .................................... 426/590, 595, 426/422, 442, 433; 210/500.1, 506

[56] References Cited

U.S. PATENT DOCUMENTS

| | | |
|---|---|---|
| 243,521 | 6/1881 | Davidson . |
| 256,082 | 4/1882 | Von Hofman . |
| 312,516 | 2/1885 | Schilling . |
| 680,889 | 8/1901 | Schutz . |
| 932,322 | 10/1909 | Jurgens et al. . |
| 1,137,265 | 4/1915 | Hübner . |
| 1,742,261 | 1/1930 | Klein . |
| 1,822,227 | 9/1931 | Lendrich et al. . |
| 2,036,345 | 4/1936 | Merkel . |
| 2,419,031 | 4/1947 | Pollack . |
| 2,518,441 | 8/1950 | Schaeppi et al. . |
| 2,626,558 | 1/1953 | Stein . |
| 2,687,355 | 8/1954 | Benner et al. . |
| 2,889,226 | 6/1959 | Hinkley . |
| 3,644,122 | 2/1972 | Yeransian . |
| 4,093,422 | 6/1978 | Hain ......................................... 23/284 |
| 4,317,841 | 3/1982 | Brambilla et al. . |
| 4,327,076 | 4/1982 | Puglia et al. . |
| 4,461,778 | 7/1984 | Vialatte née Geolier . |
| 4,755,385 | 7/1988 | Etienne et al. . |
| 4,882,181 | 11/1989 | Giddey . |
| 4,976,983 | 12/1990 | Hirsh et al. . |
| 4,980,175 | 12/1990 | Chavkin et al. . |
| 4,985,271 | 1/1991 | Neilson et al. . |
| 5,068,109 | 11/1991 | Foldager et al. . |
| 5,147,666 | 9/1992 | Doonan et al. . |
| 5,192,571 | 3/1993 | Levy . |
| 5,229,155 | 7/1993 | Weisemann et al. . |
| 5,306,511 | 4/1994 | Whang . |
| 5,350,591 | 9/1994 | Canton . |
| 5,518,743 | 5/1996 | Pergola et al. . |

FOREIGN PATENT DOCUMENTS

| | | |
|---|---|---|
| 2 027 662 | 2/1980 | United Kingdom . |
| WO 95 17826 | 7/1995 | WIPO . |

OTHER PUBLICATIONS

Barrett–Connor, E., et al., "Coffee–Associated Osteoporosis Offset by Daily Milk Consumption," *Journal of the American Medical Association*, Jan. 26, 1994, vol. 271, No. 4, pp. 280–283.

"Ground Coffee," *Consumer Reports*, Jan. 1991, pp. 30–50.

Hornstein, I., "Flavor Chemistry," symposium, American Chemical Society, Detroit, MI, 1966, pp. 180–187.

Peterson, M.S., et al., *Encyclopedia of Food Science*, 1978, pp. 1–6.

Pintauro, N., "Soluble Coffee Manufacturing Processes," Noyes Development Corp., 1969, pp. 72–73, 116–129.

Ukers, W., *Tea and Coffee Trade Journal*, 1935, pp. 292–296.

Database Abstract. AN: 86–254078 [39] WPIDS. JP 61997393, May 1986.

Database Abstract. AN: 79(10):H1669 FSTA. German 2,731,917. Inventor: Wieland, Oct. 1979.

The Condensed Chemical Dictionary, 7th Ed. pp. 575, 773, and 774, 1966.

*Primary Examiner*—Anthony J. Weier
*Attorney, Agent, or Firm*—Christensen O'Connor Johnson & Kindness PLLC

[57] ABSTRACT

A method of brewing coffee having reduced acidity is described. In the method, an acid-neutralizing composition comprising calcium carbonate, potassium hydroxide, magnesium hydroxide, and potassium chloride is utilized to produce a brewed coffee having a pH of from about 5.7 to about 6.1. A coffee product including ground coffee and an acid-neutralizing composition is also described.

7 Claims, No Drawings

BEVERAGE FILTER FOR REDUCING COFFEE ACIDITY

CROSS-REFERENCE TO RELATED APPLICATION

This application is a divisional of U.S. patent application Ser. No. 08/577,147, filed Dec. 22, 1995, now U.S. Pat. No. 5,853,787, the benefit of the priority of the filing date of which is hereby claimed under 35 U.S.C. §120.

FIELD OF THE INVENTION

The present invention relates generally to a method for reducing the acidity of acidic foods and beverages, and more specifically to a method for reducing the acidity of coffee beverages.

BACKGROUND OF THE INVENTION

The consumption of acidic food and beverages often results in physical discomfort in the form of indigestion and heartburn among other discomforts. Acidic beverages including coffees and teas are particularly troublesome because of their widespread consumption and elevated acid concentrations.

Coffee is a morning ritual for over 125 million Americans, with the average coffee drinker consuming three cups of coffee per day. However, drinking coffee does not affect all people in the same way. While some are able to drink an entire pot of coffee without experiencing any adverse effects, others may experience indigestion and discomfort. In addition to discomfort, potential health risks associated with excessive coffee consumption in general, and with caffeine consumption in particular, have been theorized. At least one study has linked coffee consumption to osteoporosis. Pregnant mothers are often cautioned to limit their intake of coffee as a precaution to ensure the health and safety of their unborn children. It is not well understood what the effects of coffee acids may be on the health of the general population, but at a minimum acidic coffee causes discomfort for many people with digestive tract disorders, such as acid reflux or ulcers.

Coffee is a complex composition derived from the brewing of roasted and ground coffee beans. The constituents of coffee beans include caffeine (1–2%), coffee oil (10–15%), sucrose and other sugars (about 8%), proteins (about 11%), ash (about 5%), and chlorogenic and caffeic acids (about 6%). Other constituents include cellulose, hemicelluloses, trigonelline, carbohydrates, volatile oils, and other acids. The composition of a particular coffee is variable and depends upon such factors as the type of bean, where the coffee is grown and harvested, and how the beans are processed. It is the individual constituents of a coffee that contribute to its natural aroma, flavor, and appeal.

Many different acidic constituents are present in coffee. Coffee's acids include malic acid, tannic acid, maleic acid, oleic acid, oxalic acid, caffeic acid and chlorogenic acid, among others. These acidic constituents are responsible for the overall acidity of coffee and the discomfort that occasionally arises from the ingestion of this acidic beverage. Furthermore, coffee contains caffeine, which, upon ingestion, causes the gastric secretion of acids. Accordingly, coffee drinking not only results in the ingestion of an acidic beverage, but also stimulates the production of additional acids.

Commonly, the coffee drinker's solution to discomfort arising from coffee's acidity is to either reduce the number of cups of coffee consumed each day, avoid drinking coffee entirely, or alternatively, dilute the coffee, or accompany coffee drinking, with dairy products such as milk or cream. Unfortunately, the use of dairy products as a solution to the problem of coffee acidity is not universal. Many people, including some coffee drinkers, suffer from lactose intolerance and have difficulty in digesting milk sugars. For these individuals, the problem of coffee acidity is not solved by the addition of milk products to coffee.

The problem of reducing the acidity of certain foods and beverages has been previously addressed. For example, a process for decreasing the malic acid content in wines involving the treatment of wine with a composition including calcium carbonate, potassium bicarbonate, and calcium tartrate has been described. U.S. Pat. No. 4,461,778. A malolactic fermentation process that provides a coffee product having reduced malic acid content has also been described. U.S. Pat. Nos. 4,976,983 and 5,147,666. A common practice in red wine production involves treating the wine with gelatin which selectively neutralizes tannic acid.

Alkaline treatments have been used in the production of coffee products. For example, in the preparation of instant coffee, coffee extracts have been treated with alkaline materials including ammonia, alkali metal and alkaline earth metal hydroxides, carbonates, and bicarbonates to improve the yield of soluble solids. U.S. Pat. No. 3,644,122. Similarly, alkaline molecular sieves have been employed in a process for improving yield in secondary coffee extracts in the production of soluble coffee. U.S. Pat. No. 5,229,155. A process for preparing a better tasting coffee involving an intermediate step of treating partially roasted coffee beans with an aqueous alkaline solution of a foodgrade base, such as sodium hydroxide, ammonium hydroxide, calcium hydroxide, or ammonium bicarbonate, prior to final roasting is also known. U.S. Pat. No. 4,986,271.

In some cultures, roasted and ground coffee is customarily brewed together with egg and eggshells. Presumably, this treatment reduces the acidity of the resulting brewed coffee. W. Ukers, *Tea and Coffee Trade Journal*, 1935. To bring out the fill flavor and strength of coffee, a coffee composition comprising a roasted coffee bean coated with alkali such as borax or bicarbonate of soda has been disclosed. U.S. Pat. No. 312,516. Today, borax is considered unsafe for human consumption, and the ingestion of sodium is often considered inadvisable for individuals on low sodium diets. An alkaline substance, lithium carbonate, has been utilized as a preserving agent for roasted and ground coffee. U.S. Pat. No. 2,419,031. A process for making coffee more digestible by raising its pH by the addition of an acid binding substance is also known. U.S. Pat. No. 2,036,345. In this process, the acid binding substance is a basic or alkaline material non-injurious to health and includes alkaline earth metal oxides, hydroxides, carbonates, and bicarbonates as well as alkali metal carbonates, bicarbonates, and alkaline phosphates. In a preferred embodiment, the acid binding substance includes trisodium phosphate and potassium bromide. Today, neither of these two ingredients is considered by the Food and Drug Administration to be Generally Regarded As Safe (GRAS).

Accordingly, despite the methods and compositions for treating coffee mentioned above, there remains a need in the art for a composition and method for reducing the acidity of foods and beverages, such as coffee, that are safe for a broad segment of the population, economical, and easy to use. The present invention addresses these needs and provides further related advantages.

SUMMARY OF THE INVENTION

Briefly, the present invention generally relates to methods of reducing the acidity of acidic foods and acidic beverages through the use of an acid-neutralling composition. More specifically, the present invention relates to methods and compositions for brewing coffee having reduced acidity. The availability of methods and compositions of this invention to the general public enables the consumer, for the first time, to adjust the acidity of any food or beverage to suit the consumer's taste. Previous methods were available only to manufacturers.

In one aspect of the invention, methods of brewing coffee having reduced acidity are disclosed. In the methods, an acid-neutralizing composition is added to a coffee product in an amount sufficient to produce a brewed coffee having a pH of from about 5.7 to about 6.1. In one embodiment, the method includes adding an acid-neutralizing composition to whole coffee beans. In another embodiment, the method includes the addition of an acid-neutralizing composition to ground coffee beans. In yet another embodiment, the method includes the addition of an acid-neutralizing composition to a brewed coffee beverage. In still another embodiment, the method includes brewing coffee utilizing a coffee filter impregnated with an acid-neutralizing composition.

In another aspect, the present invention discloses an acid-neutralizing composition. In general, the acid-neutralizing composition comprises alkaline (i.e., basic) substances and affords both rapid and long-lasting antacid activity. Suitable alkaline substances of the present invention include alkaline earth metal carbonates, alkali and alkaline earth metal hydroxides, and aluminum hydroxide. In a preferred embodiment, the alkaline substances include calcium carbonate, potassium hydroxide, and magnesium hydroxide. The acid-neutralizing composition may additionally include potassium chloride, gelatin, bacteria and fungi retarders, vitamin D, and excipients. Suitable excipients include granulating agents, dispersing agents, instant coffee, and nondairy creamers. In a particularly preferred embodiment, the acid-neutralizing composition includes calcium carbonate, potassium hydroxide, magnesium hydroxide, potassium chloride, vitamin D, and instant coffee.

In another embodiment, the present invention includes a coffee product comprised of whole coffee beans and an acid-neutralizing composition. In a further embodiment, the invention includes a coffee product comprised of ground coffee beans and an acid-neutralizing composition.

DETAILED DESCRIPTION OF THE PREFERRED EMBODIMENT

The present invention generally relates to methods and compositions useful in reducing the acidity of acidic foods and beverages. Specifically, the present invention is directed to methods and compositions for brewing coffee having reduced acidity.

In one aspect of the invention, methods of brewing coffee having reduced acidity is disclosed. In these methods, the acidity of coffee is reduced through the use of an acid-neutralizing composition. The methods of the present invention provide a brewed coffee having a pH of from about 5.7 to about 6.1. The methods are applicable to brewing methods that utilize either whole or ground coffee beans. The present invention also includes a method for reducing the acidity of a brewed coffee beverage. As noted above, the methods are also applicable to reducing the acidity of liquid foods.

In another aspect of the present invention, an acid-neutralizing composition is disclosed. The acid neutralizing composition comprises alkaline (ie., basic) substances and affords both rapid and long-lasting antacid activity. As used herein, the term "antacid activity" refers to the ability of a substance to neutralize and/or to buffer an acid. Neutralization refers to a acid-base reaction by which an acid is made neutral. Neutralization does not necessarily mean attaining neutral pH (ie., pH 7), rather, neutralization refers to the equivalence point for a particular acid-base reaction and will depend upon the respective strengths of the particular acid and base, their relative concentrations, and the buffering properties of the solution containing the acid and base. A buffer is a solution containing salts of weak acids that is capable of neutralizing both acids and bases and acts to maintain the pH of a solution. In other words, a buffered solution contains both a weak acid (e.g. acetic acid) and its conjugate weak base (e.g., sodium acetate) and its pH changes only slightly upon the addition of acid or base. The weak acid acts as a buffer when base is added to the solution, and the weak base acts as a buffer when acid is added to the solution. In the context of the present invention, the addition of an acid-neutralizing composition to an acidic food or beverage results in the neutralization of acids, thereby reducing the acidity of the food or beverage. At the same time, the food or beverage becomes buffered, that is, the pH of the food or beverage may be maintained, within limits, upon the addition of more acid.

Alkaline substances having long-lasting antacid activity include alkali and alkaline earth metal carbonates. For example, the pharmaceutical use of calcium carbonate as an effective stomach antacid is well known. The rapid antacid effect of stronger alkaline substances such as alkali and alkaline earth metal hydroxides is also known. Commonly used alkali and alkaline earth metal hydroxides include lithium, sodium, potassium, calcium, and magnesium hydroxides.

As noted above, the acid-neutralizing composition of this invention includes a combination of alkaline substances having both rapid and long-lasting antacid activity. As such, the composition of the present invention is particularly well suited for reducing the acidity of caffeinated beverages such as coffee. The rapid acting alkaline substances (e.g., potassium hydroxide and magnesium hydroxide) of the composition effectively reduce the acidity of the beverage itself, while the long-lasting alkaline substances (e.g., calcium carbonate) counteract and neutralize acidic gastric secretions stimulated by the ingestion of caffeine.

The alkaline substances of the present invention include alkaline earth metal carbonates, alkali and alkaline earth metal hydroxides, and aluminum hydroxide. More specifically, alkaline earth metal carbonates include calcium and magnesium carbonates, and alkali and alkaline earth metal hydroxides include potassium and magnesium hydroxides. In addition to alkaline substances, the acid-neutralizing composition includes potassium chloride. In a preferred embodiment, the acid-neutralizing composition comprises calcium carbonate, potassium hydroxide, magnesium hydroxide, and potassium chloride. In suitable embodiments, calcium carbonate is present in the composition in an amount ranging from about 60% to about 90% by weight of the total composition, potassium hydroxide is present in an amount ranging from about 5% to about 15% by weight of the total composition; magnesium hydroxide is present in an amount ranging from about 0.1% to about 10% by weight of the total composition; and potassium chloride is present in an amount ranging from about 1% to about 5% by weight of the total composition.

In a preferred embodiment, calcium carbonate is present in the composition in an amount ranging from about 65% to about 80% by weight of the total composition; potassium hydroxide is present in an amount ranging from about 6% to about 8% by weight of the total composition, magnesium hydroxide is present in an amount ranging from about 0.5% to about 2% by weight of the total composition; and potassium chloride is present in an amount ranging from about 2% to about 3% by weight of the total composition.

Of these acid neutraling compounds, potassium hydroxide is the most active neutralizer, effective at neutralizing maleic, oxalic, and to some extent, chlorogenic acids. The remaining compounds of the preferred composition are less active. Magnesium hydroxide supplements the neutralizing effect of the potassium hydroxide, and is the second most active neutralizer. Calcium carbonate acts as a weak neutralizer, but also serves as a diluent to provide a convenient application quantity of the composition, and as a calcium source. The potassium chloride is included primarily for flavor, providing a salty flavor to substitute for the acid flavor of untreated coffee. The combination of these ingredients of the composition provides a highly effective acid neutralizer that does not detrimentally alter the flavor of treated brewed coffee.

The alkaline substances noted above are the active ingredients primarily responsible in reducing the acidity of an acidic food or beverage. In addition to their antacid activity, the alkaline substances provide additional effects beneficial to health and nutrition. For example, magnesium hydroxide present in the composition has the effect of counteracting the constipative effect that often accompanies the ingestion of calcium carbonate. Furthermore, from a dietary standpoint, the alkaline substances also provide calcium, potassium, and magnesium, minerals for which the Food and Drug Administration has proposed minimum daily requirements.

In another embodiment of the acid-neutralizing composition, in addition to the alkaline substances noted above, the composition further includes foodgrade gelatin as an active ingredient. In a preferred embodiment, the gelatin is foodgrade, type B gelatin. Generally, for the acid-neutralizing compositions of the invention that include gelatin, gelatin is present in an amount up to about 3% by weight of the total composition. The gelatin is useful in the composition for neutralizing tannic acid, an acid present in the fruit of many plants, and one of the acids present in coffee. In a preferred embodiment, acid-neutralizing compositions that include gelatin also include a bacteria and/or fungi retarder. Suitable bacteria and/or fungi retarders include any such retarder that is effective in preventing the growth of bacteria and/or fungi in the composition. The bacteria and/or fungi retarder is present in an amount to effectively prevent the growth of bacteria and/or fungi, typically in an amount ranging from about 0.01% to about 0.2% by weight of the total composition. Preferred bacteria and/or fungi retarders include methyl paraben and propyl paraben. In one preferred embodiment, the acid-neutralizing composition includes methyl paraben in an amount ranging from about 0.01% to about 0.03% by weight of the total composition and propyl paraben in an amount ranging from about 0.07% to about 0.090% by weight of the total composition.

In addition to the alkaline substances mentioned above, the acid-neutralizing composition of this invention may include other ingredients. Thus, in another embodiment, the acid-neutraling composition includes vitamin D. Preferably, vitamin D is vitamin $D_3$ and is present in the composition in an amount ranging from about 0.1% to about 0.5% by weight of the total composition. Addition of an amount of the acid-neutralizing composition sufficient to produce a cup of coffee having a pH of from about 5.7 to about 6.1 provides a cup of coffee having about 100 IU (international units) of vitamin D. While vitamin D is not an alkaline substance useful in reducing acidity, vitamin D is active in calcium uptake. Accordingly, because of the beneficial aspects of dietary calcium (ie., recommended daily allowance of 800 to 1500 milligrams) and because the composition of this invention includes calcium as a primary ingredient, the addition of vitamin D to the composition provides further nutritional and health benefits.

The composition of this invention may also include an excipient. As used herein, the term "excipient" refers to an inert substance that forms a vehicle for the active ingredients of the composition. In the context of the present invention, suitable excipients include those that permit the effective and efficient delivery of the alkaine substances and other ingredients present in the composition of this invention, and include granulating and dispersing agents. For example, the acid-neutralizing composition may be formulated as a free-flowing solid such as a powder or granule using a granulating agent. A preferred granulating agent useful in rendering the composition a free-flowing solid is microcrystalline cellulose. Another preferred granulating agent is fumed silicon dioxide available from commercial sources (e.g., Cabot Corp., Tuscola, Ill.) and useful in controlling granule density. Furthermore, in one embodiment, the composition as a free-flowing solid is delivered to an acidic beverage where it is dispersed into solution. To assist in dispersion of the composition into solution, the composition may include a dispersing agent. A preferred dispersing agent useful for smooth dispersal of the composition in solution is carboxymethyl cellulose. In another embodiment, the excipient is soluble coffee (also known as instant coffee). In yet another embodiment, the excipient is a nondairy creamer.

In general, an excipient is present in the composition in an amount ranging from about 5% to about 30% by weight of the total composition. In a preferred embodiment, the acid-neutralizing composition includes microcrystalline cellulose in an amount from about 2% to about 10% by weight of the total composition, carboxymethyl cellulose sodium in an amount from about 2% to about 20% by weight of the total composition, and instant coffee in an amount from about 0.1% to about 0.5% by weight of the total composition. Instant coffee is suitably added to the composition to provide an appealing coffee color. Instant coffee is not required for the composition's efficacy in reducing acidity.

The acid-neutralizing composition may also be formulated as a liquid solution. When the composition is formulated as a liquid, the excipient may be water including sterile and/or distilled water.

As described above, the acid-neutralizing composition includes alkaline substances (i.e., preferably calcium carbonate, magnesium carbonate, potassium hydroxide, magnesium hydroxide, and gelatin) that are active in reducing the acidity of an acidic food or beverage; other ingredients (i.e., vitamin D) that offer additional health and nutritional benefits; and inert ingredients (i.e., potassium chloride, bacteria and/or fungi retarders, and excipients) that provide practical effectiveness relating to composition stability and formulation. All of these ingredients are Generally Regarded As Safe (GRAS) for use by the Food and Drug Administration.

Representative acid-neutralizing compositions of the present invention are described in Examples 1–3. Example 3 describes a representative acid-neutralizg composition of this invention that includes gelatin.

The acid-neutralizing composition of the present invention may be formulated in a variety of ways. As noted above, the composition may be formulated as a free-flowing solid, such as a powder or granule. The composition of the present invention may be granulated in any one of many granulation techniques known in the art. One suitable method involves the mixing of all dry components of the composition in water to form partially agglomerated clumps, followed by drying, chopping, and shifting to produce the desired granules. Other granulation methods well known to those of ordinary skill in the art include: spray drying; extrusion and chopping; grinding; the use of a fluid bed; and high shear granulation. The formulation of an acid-neutralizing composition of this invention as a free-flowing granule is described in Example 1. In addition to flowing solids, the composition may also be formulated as a pill, tablet, or capsule. The composition may also be formulated as a liquid, such as an aqueous solution, slurry, emulsion, or syrup.

The present invention also provides coffee products. In one embodiment, this invention provides a coffee product comprising whole coffee beans and an acid-neutralizing composition. In another embodiment, a coffee product comprising ground coffee beans and an acid-neutralizing composition is provided. In these coffee products, the acid-neutralizing composition is present in an amount sufficient to produce a brewed coffee having a pH of from about pH 5.7 to about 6.1. Typically, about 10 to 20 grams of the acid-neutralizing composition added to one kilogram of coffee is sufficient to produce a brewed coffee having such reduced acidity.

As noted above, one aspect of the present invention provides methods for reducing the acidity of an acidic food or beverage by the addition of an acid-neutralizing composition. In the context of this invention, acidic foods include liquid foods, such as tomato products including tomato paste, vinegar contacting products such as salad dressing, and cranberry products including cranberry sauce. Acidic beverages include any beverage having a pH less than about 4, including coffee beverages, tea beverages, and fruit juice beverages such as tomato juice and cranberry juice beverages, and citrus fruit beverages including orange and grapefruit juice beverages.

While the pH of coffee beverages will depend on many factors including the type of coffee bean, strength of the brew, and brewing conditions, the pH of most coffees falls within the range of from pH 4.8 to about pH 5.7. The present invention provides methods for reducing the acidity (i.e., increasing the pH) of coffee beverages. Preferably, the methods of the invention provide a coffee beverage having a pH in the range from about pH 5.7 to about pH 6. 1.

Generally, the present invention provides a method of brewing coffee having reduced acidity that includes adding an acid-neutralizing composition to a coffee product in an amount sufficient to produce a brewed coffee having a pH of from about pH 5.7 to about pH 6.1. In the context of the present invention, a coffee product includes whole coffee beans, ground coffee beans, and brewed coffee.

Other known processes for the deacidification of coffee include alkaline treatment of either green or semi-roasted beans at elevated temperature (e.g., 375° to 425° F.) for prolonged periods of time (e.g., 10 to 25 minutes depending upon the type of bean, its moisture content, and the roast desired). Typically, under these conditions, the deacidification is accompanied by saponification of coffee oils resulting in alteration of the coffee's flavor and aroma. To a large extent, the oils of the coffee impart its flavor and aroma.

In contrast, as described below, the methods of the present invention utilize an acid-neutralizing composition under conditions that preserve the flavor and aroma of the coffee. In the present methods, a coffee product is combined with the acid-neutralizing composition at relatively low temperature (e.g., about 220° F., the boiling point of water) for a short period of time (e.g., about 3 to 5 minutes, the time required to prepare a brewed coffee). Accordingly, the methods of this invention result in a coffee having reduced acidity without compromising the flavor, aroma, and taste integrity of the resulting brewed coffee.

In one embodiment, the present invention provides a method of brewing coffee having reduced acidity. In the method, an acid-neutralizing composition, as described above, is added to whole coffee beans to provide a whole coffee bean and acid-neutralizing composition mixture. The whole coffee bean and acid-neutralizg composition mixture is then subjected to grinding to provide a ground coffee bean and acid-neutralizing composition mixture. Finally, the ground coffee bean and an acid-neutralizing composition mixture is brewed with water to provide a brewed coffee having reduced acidity.

In this method, the reduction of acidity of a coffee beverage depends upon the quantity of the acid-neutralizing composition added to the whole coffee beans. In addition, the amount of an acid-neutralizing composition added to the whole beans will depend upon many factors including the nature and type of coffee bean. Generally, to provide a coffee beverage having reduced acidity and a pH in the range from about 5.7 to about 6.1, approximately 15 grams of the acid-neutralizng composition of this invention are added to approximately one kilogram of whole coffee beans.

In another embodiment, the present invention provides a method of brewing coffee having reduced acidity where an acid-neutralizing composition is added to ground coffee beans. In this method, the addition of an acid-neutralizing composition to ground coffee beans provides a ground coffee bean and acid-neutralizing composition mixture which is then brewed with water to provide a brewed coffee having reduced acidity.

Similar to the above method, the reduction of acidity of a coffee beverage depends upon the quantity of the acid-neutralizing composition added to the ground coffee beans, which in turn depends upon factors including the nature and type of coffee bean. Generally, to provide a coffee beverage having reduced acidity and a pH in the range from about 5.7 to about 6.1, approximately 15 grams of the acid-neutralizing composition of this invention are added to approximately one kilogram of ground coffee beans.

In yet another embodiment, this invention provides a method of preparing a coffee beverage having reduced acidity where an acid-neutralizing composition is added directly to a brewed coffee beverage. In this method, an acid-neutralizing composition is added directly to a brewed coffee, such as a cup or pot of coffee, such that the pH of the resulting brewed coffee has a pH in the range from about pH 5.7 to about pH 6.1. As noted above, the quantity of acid-neutralizing composition to effect the reduction of acidity to this preferred pH range will depend upon the acidity of a brewed coffee beverage. In general, about 100 mg of acid-neutralizing composition will increase the pH of an 8 ounce cup of coffee from about pH 5 to about pH 6. Accordingly, approximately 1.2 grams of the composition would similarly reduce the acidity of a twelve-cup pot of coffee to a pH range of about pH 5 to about pH 6.

All of the methods noted above offer the advantage that the coffee brewer may reduce the acidity of her coffee beverage to suit her own taste. Accordingly, the coffee brewer may add more or less of the acid-neutralizing composition as desired.

In still another embodiment, a method for brewing coffee having reduced acidity is provided where a coffee filter impregnated with an acid-neutralizing composition is utilized in brewing the coffee beverage. In this method, ground coffee beans are placed in a coffee filter impregnated with an acid-neutralizing composition, and the coffee is then brewed in the usual manner. The acid-neutralizing composition is present in the filter in an amount sufficient to produce a brewed coffee having a pH from about pH 5.7 to about 6.1.

The methods and compositions of the present invention provide brewed coffee having reduced acidity while at the same time maintaining the taste integrity of the coffee. Taste tests have been conducted and have demonstrated that no detrimental effect to coffee flavor occurs in the practice of the methods of the present invention. In fact, in several instances, coffees produced by these methods were rated as having a better taste than plain coffee. Some taste tests and their results are described in Example 4.

EXAMPLES

Example 1

In this example, a representative acid-neutralizing composition of the present invention is described. A method for combining the ingredients and formulating the composition as a free-flowing granule is also described.

| Ingredient | Percent by Weight |
| --- | --- |
| Calcium carbonate | 66.82 |
| Potassium hydroxide | 7.25 |
| Magnesium hydroxide | 0.67 |
| Potassium chloride | 2.67 |
| Excipient | |
| Microcrystalline cellulose (Tabulose ™, Blenver Co., Brazil) | 5.33 |
| Carboxymethyl cellulose sodium (Solutab ™, Blenver Co., Brazil) | 16.75 |
| Vitamin D (dry stabilized vitamin $D_3$-water dispersible, Vitamins, Inc., Chicago, IL) | 0.17 |
| Instant coffee (Yuban ™) | 0.35 |

A granulated formulation having the above composition was prepared as described below. To a 20 quart mixing bowl was added 3675 grams calcium carbonate, 37 grams magnesium hydroxide, 147 grams potassium chloride, 293 grams Tabulosez™, 921 grams Solutab™, and 9 grams vitamin $D_3$-water dispersible. The contents of the mixing bowl were mixed for approximately 5 minutes. While mixing, a solution of 399 grams potassium hydroxide in about 400 mL of deionized water was delivered over a period of about 2 minutes to the mixed solids in the mixing bowl by way of a peristaltic pump. Upon the completion of the addition of the potassium hydroxide solution, the blend was mixed for an additional ten minutes. A solution of 19 grams instant coffee (Yuban™) in 1200 mL deionized water (prepared from the addition of 1200 mL hot deionized water to 19 grams instant coffee) was then delivered over a period of about 4.5 minutes to the mixed solids in the mixing bowl by way of a peristaltic pump. Upon the completion of the addition of the instant coffee solution, the blend was mixed for an additional five minutes. At this point, 100 to 200 mL additional water may be added to the blend, if necessary, to provide a mixture having a granular (i.e., nonpowdery) appearance. The moist formula was then mixed for approximately 20 minutes with occasional wiping of the sides of the mixing bowl with a spatula to assure a thorough mixing of the entire formula. After thorough mixing, the moist formula was transferred into a large plastic bin. The contents of the bin were then added in portions to fill the funnel of a cutting machine. The cutting machine and the auger were then powered on and the formula was granulated. After granulation, the cutting machine and auger were powered off and the granulated formula was collected using a vacuum. The granulated formula was then distributed to oven trays (approximately one pound of formula per tray), the trays were placed in an oven, and the formula dried for 30 minutes at a temperature of 180° F. The trays of formula were then rotated in the oven to assure uniform heat treatment, and dried for an additional 30 minutes. Removal from the oven and cooling provided a representative composition of the present invention formulated as a free-flowing granule.

Example 2

In this example, another representative acid-neutralizing composition of the present invention is described.

| Ingredient | Percent by Weight |
| --- | --- |
| Calcium carbonate | 63.33 |
| Potassium hydroxide | 11.64 |
| Magnesium hydroxide | 6.14 |
| Potassium chloride | 2.33 |
| Excipient | |
| Microcrystalline cellulose (Tabulose ™, Blenver Co., Brazil) | 6.19 |
| Carboxymethyl cellulose sodium (Solutab ™, Blenver Co., Brazil) | 8.91 |
| Vitamin D (dry stabilized vitamin $D_3$-water dispersible, Vitamins, Inc., Chicago, IL) | 0.47 |
| Magnesium stearate | 1.01 |

These ingredients were combined to provide a composition that is a free-flowing granule by the method described above in Example 1.

Example 3

In this example, a representative acid-neutralizing composition of the present invention including gelatin and bacteria and fungi retarder is described.

| Ingredient | Percent by Weight |
| --- | --- |
| Calcium carbonate | 62.10 |
| Potassium hydroxide | 11.42 |
| Magnesium hydroxide | 6.02 |
| Potassium chloride | 2.28 |
| Foodgrade type B gelatin | 1.83 |
| Bacteria and fungi retarder | |
| Methyl paraben | 0.02 |
| Propyl paraben | 0.08 |
| Excipient | |
| Microcrystalline cellulose (Tabulose ™, Blenver Co., Brazil) | 6.07 |
| Carboxymethyl cellulose sodium (Solutab ™, Blenver Co., Brazil) | 8.74 |

| Ingredient | Percent by Weight |
| --- | --- |
| Vitamin D (dry stabilized vitamin $D_3$-water dispersible, Vitamins, Inc., Chicago, IL) | 0.46 |
| Magnesium stearate | 1.00 |

These ingredients were combined to provide a composition that is a free-flowing granule by the method described above in Example 1.

Example 4

In this example, tests evaluating the taste of coffees prepared by the methods of the present invention are described. In these tests, the taste of coffees containing embodiments of the acid-neutralizing compositions of this invention was evaluated by coffee tasters and compared with the taste of plain coffee (i.e., the same coffee containing no acid-neutralizing composition).

In the tests, the coffee tasters rated each of nine categories on a scale from 1 (worst) to 5 (best). The categories evaluated were aroma, appearance, acidic taste, chemical taste, salt taste, sweetness, bitterness, aftertaste, and overall impression.

The following acid-neutralizing composition formulations were tested:

Formulation A:
  567 grams calcium carbonate
  28.4 grams FMA-11™ (a mixture consisting of 41.5 weight percent aluminum hydroxide, 8.0 weight percent magnesium hydroxide, 50.5 weight percent calcium carbonate; Reheis Corp., Berkeley Heights, N.J.)
  6 grams potassium chloride
  6 grams gelatin Formulation B:
  143.5 grams calcium carbonate
  3.5 grams FMA-11™
  1.8 grams aluminum hydroxide
  1.5 grams potassium chloride Formulation C:
  143.5 grams calcium carbonate
  3.5 grams FMA-11™
  1.8 grams magnesium carbonate
  1.5 grams potassium chloride Formulation D:
  140.3 grams calcium carbonate
  7.1 grams FMA-11™
  3 grams potassium chloride Formulation E:
  138.8 grams calcium carbonate
  7.1 grams FMA-11™
  4.5 grams potassium chloride Formulation F:
  137.3 grams calcium carbonate
  7.1 grams FMA-11™
  6 grams potassium chloride Each of the test coffee samples was prepared by the addition of 1.4 grams of one of the above formulations to a 12 cup pot of brewed coffee Millstone BreakfastBlend™.

The taste test results are summarized in the following table. Average score refers to the average overall taste on a scale from 1 (worst) to 5 (best).

| Formulation | Average score |
| --- | --- |
| Plain coffee | 3.8 (2.75) |
| A | 3.8 (2.34) |
| B | 4.3 (3.00) |
| C | 3.6 (2.88) |
| D | 3.9 (2.86) |
| E | 3.4 |
| F | 3.1 |

The values represent an average of the values assigned by eight taste testers in the age group of 25 to 35 years old.

The values in parentheses represent the results of a subsequent taste test by eight taste testers in the age group of 55 to 75 years old.

As summarized in the table above, several acid-neutralizing composition formulations were found to have tastes more pleasing than plain coffee. In the taste tests, Formulation B was determined to be the most flavorful coffee.

While the preferred embodiment of the invention has been illustrated and described, it will be appreciated that various changes can be made therein without departing from the spirit and scope of the invention.

What is claimed is:

1. A beverage filter impregnated with an acid-neutralizing composition, wherein the filter is adapted to be received in a fresh coffee brewing receptacle, and wherein the acid-neutralizing composition is at least partially soluble in water.

2. The beverage filter of claim 1 wherein the acid-neutralizing composition comprises calcium carbonate, potassium hydroxide, magnesium hydroxide, and potassium chloride.

3. The beverage filter of claim 1 wherein the acid-neutralizing composition comprises an alkaline substance selected from the group consisting of an alkaline earth metal carbonate, an alkaline earth metal hydroxide, an alkali metal hydroxide, and mixtures thereof.

4. The beverage filter of claim 3 wherein the alkaline earth metal carbonate is selected from the group consisting of calcium carbonate and magnesium carbonate.

5. The beverage filter of claim 3 wherein the alkaline earth metal hydroxide comprises magnesium hydroxide.

6. The beverage filter of claim 3 wherein the alkali metal hydroxide comprises potassium hydroxide.

7. The beverage filter of claim 1 wherein the acid-neutralizing composition comprises potassium hydroxide.

* * * * *

UNITED STATES PATENT AND TRADEMARK OFFICE
CERTIFICATE OF CORRECTION

PATENT NO. : 6,102,213
DATED : August 15, 2000
INVENTOR(S) : I.M. Gurol

It is certified that error appears in the above-identified patent and that said Letters Patent is hereby corrected as shown below:

COLUMN        LINE

[56]              (U.S.           "IIain" should read --Hain--
Pg. 1, col. 1     Patents,
                  Item 16)

Signed and Sealed this

Twenty-ninth Day of May, 2001

Attest:

NICHOLAS P. GODICI

Attesting Officer    Acting Director of the United States Patent and Trademark Office